United States Patent
Vogelstein et al.

(10) Patent No.: US 12,116,628 B2
(45) Date of Patent: *Oct. 15, 2024

(54) RAPID ANEUPLOIDY DETECTION

(71) Applicant: The Johns Hopkins University, Baltimore, MD (US)

(72) Inventors: Bert Vogelstein, Baltimore, MD (US); Kenneth W. Kinzler, Baltimore, MD (US); Nickolas Papadopoulos, Towson, MD (US); Isaac A. Kinde, Beaumont, CA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/483,537

(22) Filed: Sep. 23, 2021

(65) Prior Publication Data
US 2022/0010371 A1   Jan. 13, 2022

Related U.S. Application Data (63) Continuation of application No. 14/792,716, filed on Jul. 7, 2015, now abandoned, which is a continuation of application No. 14/388,314, filed as application No. PCT/US2013/033451 on Mar. 22, 2013, now Pat. No. 10,053,729.

(60) Provisional application No. 61/659,695, filed on Jun. 14, 2012, provisional application No. 61/615,535, filed on Mar. 26, 2012.

(51) Int. Cl.
| | | |
|---|---|---|
| *C12Q 1/68* | (2018.01) | |
| *C12Q 1/6811* | (2018.01) | |
| *C12Q 1/6827* | (2018.01) | |
| *C12Q 1/6869* | (2018.01) | |
| *C12Q 1/6883* | (2018.01) | |

(52) U.S. Cl.
CPC .......... *C12Q 1/6869* (2013.01); *C12Q 1/6811* (2013.01); *C12Q 1/6827* (2013.01); *C12Q 1/6883* (2013.01); *C12Q 2600/112* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 6,258,540 B1 | 7/2001 | Lo |
| 7,332,277 B2 | 2/2008 | Dhallan |
| 7,537,889 B2 | 5/2009 | Sinha et al. |
| 7,645,576 B2 | 1/2010 | Lo |
| 7,709,194 B2 | 5/2010 | Lo |
| 7,888,017 B2 | 2/2011 | Quake et al. |
| 8,137,912 B2 | 3/2012 | Kapur |
| 2004/0081996 A1* | 4/2004 | Landers ................. G16B 20/20 435/6.11 |
| 2004/0096892 A1* | 5/2004 | Wang .................... C12Q 1/6841 435/6.13 |
| 2006/0019270 A1* | 1/2006 | Yang .................... C12Q 1/6827 435/6.12 |
| 2006/0172294 A1* | 8/2006 | Petronis .............. C12Q 1/6883 435/6.12 |
| 2008/0138809 A1 | 6/2008 | Kapur et al. |
| 2008/0228589 A1* | 9/2008 | Koehler ................. G16B 50/10 705/26.5 |
| 2009/0029377 A1* | 1/2009 | Lo ........................ C12Q 1/6827 702/20 |
| 2010/0105049 A1* | 4/2010 | Ehrich ............... G01N 33/5308 435/6.12 |
| 2010/0138165 A1* | 6/2010 | Fan ...................... C12Q 1/6883 702/20 |
| 2012/0003637 A1 | 1/2012 | Lo et al. |
| 2015/0051085 A1 | 2/2015 | Vogelstein et al. |
| 2015/0376691 A1 | 12/2015 | Vogelstein et al. |

FOREIGN PATENT DOCUMENTS

| | | | | |
|---|---|---|---|---|
| CA | 2439332 | | 9/2002 | |
| CA | 2645045 | | 9/2007 | |
| EP | 2261371 | | 12/2010 | |
| WO | WO 2005/023091 | | 3/2005 | |
| WO | WO 2005/035725 | | 4/2005 | |
| WO | WO 2009/013496 | | 1/2009 | |
| WO | WO 2011/018600 | | 2/2011 | |
| WO | WO-2011066476 A1 * | 6/2011 | .......... B01F 13/0062 |
| WO | WO 2011/087760 | | 7/2011 | |

(Continued)

OTHER PUBLICATIONS

Boissinot, S., et al. The insertional history of an active family of L1 retrotransposons in humans. Genome Research, vol. 14, p. 1221-1231, 2004.*

American College of Obstetricians and Gynecologists, "Invasive prenatal testing for aneuploidy," ACOG Practice Bulletin No. 88 Obstetrics & Gynecol., Dec. 2007, 110(6):1459-67.

Bianchi et al., "Genome-wide fetal aneuploidy detection by maternal plasma DNA sequencing," Obstetrics & Gynecol., May 2012, 119(5):890-901. doi: 10.1097/AOG.0b013e31824fb482.

Bolstad et al., "A comparison of normalization methods for high density oligonucleolide array data based on variance and bias," Bioinformatics, Jan. 2003, 22;19(2):185-93.

(Continued)

*Primary Examiner* — Suryaprabha Chunduru (74) *Attorney, Agent, or Firm* — Fish & Richardson P.C.

(57) ABSTRACT

Massively parallel sequencing of cell-free, maternal plasma DNA was recently demonstrated to be a safe and effective screening method for fetal chromosomal aneuploidies. Here, we report an improved sequencing method achieving significantly increased throughput and decreased cost by replacing laborious sequencing library preparation steps with PCR employing a single primer pair. Using this approach, samples containing as little as 4% trisomy 21 DNA could be readily distinguished from euploid samples.

12 Claims, 10 Drawing Sheets

(56) References Cited

FOREIGN PATENT DOCUMENTS

| WO | WO 2011/090559 | 7/2011 |
|---|---|---|
| WO | WO 2011/142836 | 11/2011 |
| WO | WO 2013/148496 | 10/2013 |

OTHER PUBLICATIONS

Bustamante-Aragones et al., Non-invasive prenatal diagnosis of single-gene disorders from maternal blood. Gene, Aug. 2012, 1:504(1):144-9. doi: 10.1016/j.gene.2012.04.045. Epub Apr. 25, 2012.

Canadian Office Action in Application No. 2868836, dated Jun. 28, 2017, 8 pages.

Chen et al., "Noninvasive prenatal diagnosis of fetal trisomy 18 and trisomy 13 by maternal plasma DNA sequencing," PLoS One. 2011; 6(7):e21791. doi: 10.1371/journal.pone.0021791. Epub Jul. 6, 2011.

Chiu et al., "Noninvasive prenatal diagnosis empowered by high-throughput sequencing," Prenat Diagn., Apr. 2012, 32(4):401-6. doi: 10.1002/pd.3822.

Chiu et al., "Maternal plasma DNA analysis with massively parallel sequencing by ligation for noninvasive prenatal diagnosis of trisomy 21," Clin Chem. Mar. 2010; 56(3):459-63. doi: 10.1373/clinchem.2009.136507. Epub Dec. 21, 2009.

Chiu et al., "Noninvasive prenatal diagnosis of fetal chromosomal aneuploidy by massively parallel genomic sequencing of DNA in maternal plasma" PNAS, Dec. 2008,105:51:20458-20463.

Cleary-Goldman et al., "Impact of maternal age on obstetric outcome," Obstet Gynecol, May 2005, 105(5 Pt 1):983-90.

Dan et al., "Prenatal detection of aneuploidy and imbalanced chromosomal arrangements by massively parallel sequencing," PLoS One. 2012; 7(2):e27835. doi: 10.1371/journal.pone.0027835. Epub Feb. 28, 2012.

Ehrich et al., "Noninvasive detection of fetal trisomy 21 by sequencing of DNA in maternal blood: a study in a clinical setting," Am J Obslet Gynecol., Mar. 2011, 204(3):205.el-11. doi: 10.1016/j.ajog.2010.12.060. Epub Feb. 18, 2011.

Extended European Search Report issued in related European Application No. 13768366.0, dated Nov. 30, 2015.

Fan et al., "Noninvasive diagnosis of fetal aneuploidy by shotgun sequencing DNA from maternal blood," PNAS, Oct. 21, 2008, 105(42):16266-16271.

Fan et al., "Sensitivity of Noninvasive Prenatal Detection of Fetal Aneuploidy from Maternal Plasma Using Shotgun Sequencing is Limited Only by Counting Statistics," PLoS One, vol. 5, No. 5, Jan. 1, 2010.

Fujita et al., "The UCSC Genome Browser database: update 2011,"Nucleic Acids Res. Jan. 2011, 39(Database issue):D876-82. doi: 10.1093/nar/gkq963. Epub Oct. 18, 2010.

Haissam, R. et al. "Rapid detection of common autosomal aneuploidies by quantitative fluorescent PCR on uncultured amniocytes," European Journal of Human Genetics, 2002, 10:462-466.

International Search Report and Written Opinion mailed Jul. 12, 2013, for PCT/US2013/033451.

Israelian Office Action in Israel Patent Application No. 234850, dated May 11, 2017.

Kent et al., "BLAT—the BLAST-like alignment tool," Genome Res., Apr. 2002, 12(4):656-64.

Kinde et al., "Detection and quantification of rare mutations with massively parallel sequencing," Proc Nall Acad Sci US A., Jun. 2011, 7; 108(23):9530-5. doi: 10.1073/pnas.1105422108. Epub May 17, 2011.

Kubota et al., "In silica genomic subtraction guides development of highly accurate, DNA-based diagnostics for Ralstonia solanacearum race 3 biovar 2 and blood disease bacterium" Journal of General Plant Pathology, Mar. 2011, 77:3:182-193.

Kuhn et al., The UCSC genome browser database: update 2007, Nucleic Acids Res. Jan. 2007, 35(Database issue):D668-73. Epub Nov. 16, 2006.

Lander et al., "Initial sequencing and analysis of the human genome,"Nature. Feb. 2001 409(6822):860-921.

Langmead et al., "Ultrafast and memory-efficient alignment of short DNA sequences to the human genome," Genome Biol., 2009; 10(3):R25. doi: 10.1186/GB-2009-10-3-r25. Epub Mar. 4, 2009.

Lo et al., Quantitative analysis of fetal DNA in maternal plasma and serum: implications for noninvasive prenatal diagnosis. Am J Hum Genet. Apr. 1998, 62(4):768-75.

Mutter et al., "Molecular diagnosis of sex chromosome aneuploidy using quantitative PCR.", Nuckeic Acids Res., vol. 19 (15), p. 4203-4207, 1991.

Office Action issued in related Australian Application No. 2013240088, dated May 6, 2016.

Palomaki et al (2011) DNA sequencing of maternal plasma to detect Down syndrome: an international clinical validation study. Genet Med. Nov. 2011; 13(11):913-20. doi: 10.1097/GIM.0b013e3182368a0e.

Rahil et al., "Rapid detection of common autosomal aneuploidies by quantitative fluorescent PCR on uncultured amniocytes," European Journal of Human Genetics, (2002), 10, 462-466.

Resta et al (2005) Changing demographics of advanced maternal age (AMA) and the impact on the predicted incidence of Down syndrome in the United States: Implications for prenatal screening and genetic counseling. Am J Med Genet A. Feb. 15, 2005; 133A (1):31-6.

Slater et al., "Rapid, high throughput prenatal detection of aneuploidy using a novel quantitative method (MLPA).", J. Med. Genetics, vol. 40, p. 907-912, 2003.

Smit et al (1999) Interspersed repeats and other mementos of transposable elements in mammalian genomes. Curr Opin Genet Dev. Dec. 1999; 9(6):657-63.

Sparks, AB., et al., "Selective analysis of cell-free DNA in maternal blood for evaluation of fetal trisomy," Prenatal Diagnosis, vol. 32, pp. 3-9, 2012.

Staebler et al., "Should determination of the karyotype be systematic for all malformations detected by obstetrical ultrasound?" Prenat Diagn., Jul. 2005, 25(7):567-73.

Stumm et al., "Noninvasive prenatal detection of chromosomal aneuploidies using different next generation sequencing strategies and algorithms," Prenat Diagn., Jun. 2012 32(6):569-77. doi: 10.1002/pd.3862. Epub May 9, 2012.

Vogelstein et al., "Digital PCR." Proc Nall Acad Sci U SA. Aug. 1999, 3; 96(16):9236-41.

Wang et al., "Digital karyotyping," Proc Natl Acad Sci US A., Dec. 2002, 10; 99(25):16156-61. Epub Dec. 2, 2002.

Xiong et al., "COBRA: a sensitive and quantitative DNA methylation assay," Nuc .. Acids. Res., 1997, 25:12:2532-2534.

Extended Search Report in European Appln. No. 23170939.5, dated Oct. 11, 2023, 6 pages.

Ledbetter et al., "Rapid Isolation of DNA Probes within Specific Chromosome Regions by Interspersed Repetitive Sequence Polymerase Chain Reaction," Genomics, Mar. 1990, 6(3):475-481.

Mouliere et al., "Circulating tumor-derived DNA is shorter than somatic DNA in plasma," Proc. Nat. Acad. Sci. USA, Mar. 17, 2015, 112(11):3178-3179.

* cited by examiner

SUPPLEMENTARY TABLE 1: SAMPLES ANALYZED IN THIS FAST-SeqS STUDY

| INDIVIDUAL | TISSUE | ANEUPLOIDY | SAMPLE NAME |
|---|---|---|---|
| n_01 | Plasma | None | n_01_pls |
| n_02 | Plasma | None | n_02_pls |
| n_03_1 | Plasma | None | n_03_1_pls |
| n_03_2 | Plasma | None | n_03_2_pls |
| n_04 | Plasma | None | n_04_pls |
| n_05 | Plasma | None | n_05_pls |
| n_06 | Plasma | None | n_06_pls |
| n_07 | Plasma | None | n_07_pls |
| n_01 | WBC | None | n_01_wbc |
| n_02 | WBC | None | n_02_wbc |
| n_03_1 | WBC | None | n_03_1_wbc |
| n_03_2 | WBC | None | n_03_2_wbc |
| n_04 | WBC | None | n_04_wbc |
| n_05 | WBC | None | n_05_wbc |
| n_06 | WBC | None | n_06_wbc |
| n_07 | WBC | None | n_07_wbc |
| n_08 | Spleen | None | n_08 |
| n_09 | Spleen | None | n_09 |
| n_10 | Spleen | None | n_10 |
| n_11 | Spleen | None | n_11 |
| n_12 | Spleen | None | n_12 |
| n_13 | Spleen | None | n_13 |
| n_14 | Spleen | None | n_14 |
| n_15 | WBC | None | n_15 |
| t21_01 | Fibroblast | Trisomy 21 (NA02767) | t21_01 |
| t21_02 | Fibroblast | Trisomy 21 (NA04616) | t21_02 |
| t21_03 | Fibroblast | Trisomy 21 (NG05120) | t21_03 |
| t21_04 | Fibroblast | Trisomy 21 (NG05397) | t21_04 |
| t21_05 | Fibroblast | Trisomy 21 (NG07438) | t21_05 |
| t18_01 | Fibroblast | Trisomy 18 (NA03623) | t18_01 |
| t18_02 | Fibroblast | Trisomy 18 (NG12614) | t18_02 |
| t13_01 | Fibroblast | Trisomy 13 (NA03330) | t13_01 |

FIG. 5

SUPPLEMENTARY TABLE 2: SEQUENCING CHARACTERISTICS OF FAST-SeqS EXPERIMENTS

| ILLUMINA INSTRUMENT | SAMPLE(S) SEQUENCED | GROUP | EXP. ID | SAMPLES PER LANE | TAGS PASSING CHASTITY FILTER | UNIQUE ALIGNMENTS | UNIQUE ALIGNMENTS (%) | DISTINCT POSITIONS |
|---|---|---|---|---|---|---|---|---|
| HiSeq 2000 | n_01_pls | 1 | 1 | 4 | 27,179,424 | 8,303,313 | 31% | 22,589 |
| HiSeq 2000 | n_02_pls | 1 | 2 | 4 | 29,081,731 | 10,081,137 | 35% | 23,632 |
| HiSeq 2000 | n_03_1_pls | 1 | 3 | 4 | 30,074,519 | 10,205,766 | 34% | 23,608 |
| HiSeq 2000 | n_03_2_pls | 1 | 4 | 4 | 34,968,939 | 12,626,577 | 36% | 24,562 |
| HiSeq 2000 | n_04_pls | 1 | 5 | 4 | 30,842,018 | 10,492,951 | 34% | 24,163 |
| HiSeq 2000 | n_05_pls | 1 | 6 | 4 | 36,048,017 | 12,997,372 | 36% | 24,314 |
| HiSeq 2000 | n_06_pls | 1 | 7 | 4 | 32,670,848 | 11,536,414 | 35% | 23,145 |
| HiSeq 2000 | n_07_pls | 1 | 8 | 4 | 31,518,407 | 11,526,042 | 37% | 23,431 |
| HiSeq 2000 | n_01_wbc | 2 | 9 | 4 | 35,712,331 | 11,805,456 | 33% | 22,807 |
| HiSeq 2000 | n_02_wbc | 2 | 10 | 4 | 13,158,351 | 4,905,067 | 37% | 20,577 |
| HiSeq 2000 | n_03_1_wbc | 2 | 11 | 4 | 42,674,992 | 16,015,347 | 38% | 23,454 |
| HiSeq 2000 | n_03_2_wbc | 2 | 12 | 4 | 19,063,243 | 7,556,803 | 40% | 21,133 |
| HiSeq 2000 | n_04_wbc | 2 | 13 | 4 | 39,854,363 | 14,576,619 | 37% | 23,285 |
| HiSeq 2000 | n_05_wbc | 2 | 14 | 4 | 25,058,110 | 9,607,768 | 38% | 21,642 |
| HiSeq 2000 | n_06_wbc | 2 | 15 | 4 | 31,447,494 | 11,781,575 | 37% | 22,255 |
| HiSeq 2000 | n_07_wbc | 2 | 16 | 4 | 27,035,516 | 10,435,840 | 39% | 21,828 |
| GA IIx | n_08 | 3 | 17 | 2.00 | 11,233,449 | 4,002,305 | 36% | 20,873 |
| GA IIx | n_09 | 3 | 18 | 2.00 | 10,593,346 | 4,430,374 | 42% | 20,804 |
| GA IIx | n_10 | 3 | 19 | 2.00 | 9,015,697 | 3,909,552 | 43% | 20,392 |
| GA IIx | n_11 | 3 | 20 | 2.00 | 9,976,099 | 4,381,161 | 44% | 20,581 |
| GA IIx | n_12 | 3 | 21 | 2.00 | 9,698,517 | 4,380,884 | 45% | 20,466 |
| GA IIx | n_13 | 3 | 22 | 2.00 | 10,432,676 | 4,645,608 | 45% | 20,737 |
| GA IIx | n_14 | 3 | 23 | 2.00 | 7,871,040 | 3,514,064 | 45% | 20,135 |
| GA IIx | n_15 | 3 | 24 | 2.00 | 8,198,416 | 2,847,661 | 35% | 20,046 |
| GA IIx | t21_01 | 3 | 25 | 2.00 | 10,381,557 | 3,515,217 | 34% | 20,595 |
| GA IIx | t21_02 | 3 | 26 | 2.00 | 7,939,433 | 2,911,392 | 37% | 20,163 |
| GA IIx | t21_03 | 3 | 27 | 2.00 | 5,524,580 | 1,972,803 | 36% | 19,095 |
| GA IIx | t21_04 | 3 | 28 | 2.00 | 6,476,900 | 2,326,116 | 36% | 19,653 |
| GA IIx | t18_01 | 3 | 29 | 2.00 | 3,716,461 | 1,343,382 | 36% | 18,484 |
| GA IIx | t18_02 | 3 | 30 | 2.00 | 6,197,319 | 2,384,437 | 38% | 19,543 |
| GA IIx | t13_01 | 3 | 31 | 2.00 | 7,373,315 | 2,598,029 | 35% | 19,809 |
| GA IIx | 100% n_15 | 4 | 32 | 2.00 | 9,905,447 | 3,964,677 | 40% | 20,612 |
| GA IIx | 100% n_15 | 4 | 33 | 2.00 | 10,540,366 | 3,412,883 | 32% | 20,674 |
| GA IIx | 95% n_15 + 5% t21_05 | 4 | 34 | 2.00 | 10,618,558 | 4,243,752 | 40% | 21,136 |
| GA IIx | 95% n_15 + 5% t21_05 | 4 | 35 | 2.00 | 10,713,550 | 4,261,765 | 40% | 21,095 |
| GA IIx | 90% n_15 + 10% t21_05 | 4 | 36 | 2.00 | 11,170,581 | 4,453,489 | 40% | 21,030 |
| GA IIx | 75% n_15 + 25% t21_05 | 4 | 37 | 2.00 | 9,444,369 | 3,761,988 | 40% | 20,950 |
| HiSeq 2000 | 100% n_15 | 5 | 38 | 4.00 | 29,844,141 | 10,239,086 | 34% | 22,194 |
| HiSeq 2000 | 100% n_15 | 5 | 39 | 4.00 | 36,518,106 | 13,771,732 | 38% | 23,612 |
| HiSeq 2000 | 100% n_15 | 5 | 40 | 4.00 | 29,971,627 | 11,108,083 | 37% | 22,689 |

FIG. 6A

| | | | | | | | | |
|---|---|---|---|---|---|---|---|---|
| HiSeq 2000 | 100% n_15 | 5 | 41 | 4.00 | 42,240,580 | 15,998,021 | 38% | 23,436 |
| HiSeq 2000 | 96% n_15 + 4% t21_05 | 5 | 42 | 4.00 | 22,779,370 | 7,992,518 | 35% | 21,374 |
| HiSeq 2000 | 96% n_15 + 4% t21_05 | 5 | 43 | 4.00 | 20,583,900 | 8,066,490 | 39% | 21,822 |
| HiSeq 2000 | 96% n_15 + 4% t21_05 | 5 | 44 | 4.00 | 13,435,012 | 5,239,203 | 39% | 20,555 |
| HiSeq 2000 | 96% n_15 + 4% t21_05 | 5 | 45 | 4.00 | 16,988,321 | 6,752,178 | 40% | 21,053 |
| HiSeq 2000 | 92% n_15 + 8% t21_05 | 5 | 46 | 4.00 | 31,696,544 | 10,785,467 | 34% | 22,376 |
| HiSeq 2000 | 92% n_15 + 8% t21_05 | 5 | 47 | 4.00 | 33,552,046 | 12,537,527 | 37% | 23,710 |
| HiSeq 2000 | 92% n_15 + 8% t21_05 | 5 | 48 | 4.00 | 31,650,369 | 11,635,853 | 37% | 22,784 |
| HiSeq 2000 | 92% n_15 + 8% t21_05 | 5 | 49 | 4.00 | 37,499,259 | 14,062,747 | 38% | 23,228 |

FIG. 6B

SUPPLEMENTARY TABLE 3: OLIGONUCLEOTIDES USED TO PREPARE AND SEQUENCE FAST-SeqS SAMPLES

| PRIMER NAME | SEQUENCE |
|---|---|
| ROUND-1 FOR-1 | CGACGTAAAACGACGGCCAGTNNNNNNNNNNNNNNNNNNACACAGGGAGGGGAACAT |
| ROUND-1 FOR-2 | CGACGTAAAACGACGGCCAGTHBVDHBVDHBVDHBVDHBVDACACAGGGAGGGGAACAT |
| ROUND-1 REV | CACACAGGAAACAGCTATGACCATGTGCCATGGTGGTTTGCT |
| ROUND-2 FOR | AATGATACGGCGACCACCGAGATCTACACCGACGTAAAACGACGGCCAGT |
| ROUND-2 REV-1 | CAAGCAGAAGACGGCATACGAGATCATCAGCACACAGGAAACAGCTATGACCATG |
| ROUND-2 REV-2 | CAAGCAGAAGACGGCATACGAGATGCCAATCACACAGGAAACAGCTATGACCATG |
| ROUND-2 REV-3 | CAAGCAGAAGACGGCATACGAGATTGACCACACACAGGAAACAGCTATGACCATG |
| ROUND-2 REV-4 | CAAGCAGAAGACGGCATACGAGATTTAGGCCACACAGGAAACAGCTATGACCATG |
| ROUND-2 REV-5 | CAAGCAGAAGACGGCATACGAGATCTTGTACACACAGGAAACAGCTATGACCATG |
| UNIVERSAL SEQUENCING PRIMER | GAGATCTACACCGACGTAAAACGACGGCCAGT |
| INDEX SEQUENCING PRIMER | CATGGTCATAGCTGTTTCCTGTGTG |

LEGEND:

FAST-1 SEQUENCE

UNIQUE IDENTIFIER

UNIVERSAL PRIMER SEQUENCE

INDEX SEQUENCE

ILLUMINA GRAFTING SEQUENCE

FIG. 7

TABLE 1 - SAMPLES ANALYZED IN THIS FAST-SeqS STUDY

| INDIVIDUAL | TISSUE | ANEUPLOIDY | SAMPLE NAME |
|---|---|---|---|
| n_01 | Plasma | None | n_01_pls |
| n_02 | Plasma | None | n_02_pls |
| n_03_1 | Plasma | None | n_03_1_pls |
| n_03_2 | Plasma | None | n_03_2_pls |
| n_04 | Plasma | None | n_04_pls |
| n_05 | Plasma | None | n_05_pls |
| n_06 | Plasma | None | n_06_pls |
| n_07 | Plasma | None | n_07_pls |
| n_01 | WBC | None | n_01_wbc |
| n_02 | WBC | None | n_02_wbc |
| n_03_1 | WBC | None | n_03_1_wbc |
| n_03_2 | WBC | None | n_03_2_wbc |
| n_04 | WBC | None | n_04_wbc |
| n_05 | WBC | None | n_05_wbc |
| n_06 | WBC | None | n_06_wbc |
| n_07 | WBC | None | n_07_wbc |
| n_08 | Spleen | None | n_08 |
| n_09 | Spleen | None | n_09 |
| n_10 | Spleen | None | n_10 |
| n_11 | Spleen | None | n_11 |
| n_12 | Spleen | None | n_12 |
| n_13 | Spleen | None | n_13 |
| n_14 | Spleen | None | n_14 |
| n_15 | WBC | None | n_15 |
| t21_01 | Fibroblast | Trisomy 21 (NA02767) | t21_01 |
| t21_02 | Fibroblast | Trisomy 21 (NA04616) | t21_02 |
| t21_03 | Fibroblast | Trisomy 21 (NG05120) | t21_03 |
| t21_04 | Fibroblast | Trisomy 21 (NG05397) | t21_04 |
| t21_05 | Fibroblast | Trisomy 21 (NG07438) | t21_05 |
| t18_01 | Fibroblast | Trisomy 18 (NA03623) | t18_01 |
| t18_02 | Fibroblast | Trisomy 18 (NG12614) | t18_02 |
| t13_01 | Fibroblast | Trisomy 13 (NA03330) | t13_01 |

FIG. 8

RAPID ANEUPLOIDY DETECTION

CROSS REFERENCE TO RELATED APPLICATIONS

This application is a continuation of U.S. application Ser. No. 14/792,716, filed Jul. 7, 2015, which is a continuation of U.S. application Ser. No. 14/388,314, filed Sep. 26, 2014, now U.S. Pat. No. 10,053,729, issued on Aug. 21, 2018, which is a National Stage application under 35 U.S.C. § 371 of International Application No. PCT/US2013/033451, having an International Filing Date of Mar. 22, 2013, which claims the benefit of priority of U.S. Provisional Application No. 61/659,695, filed Jun. 14, 2012, and U.S. Provisional Application No. 61/615,535, filed Mar. 26, 2012, each of which are incorporated herein by reference in their entirety.

This invention was made with government support under grant CA043460, CA057345 and CA062924 awarded by the National Institutes of Health. The government has certain rights in the invention.

TECHNICAL FIELD OF THE INVENTION

This invention is related to the area of genetic analysis. In particular, it relates to assessment of relative copy number of chromosomal sequences.

BACKGROUND OF THE INVENTION

A major chromosomal abnormality is detected in approximately 1 of 140 live birth[1] and in a much higher fraction of fetuses that do not reach term or are still-born[2]. The most common aneuploidy is trisomy 21, which currently occurs in 1 of 730 births[1]. Though less common than trisomy 21, trisomy 18 (Edwards Syndrome) and trisomy 13 (Patau syndrome) occur in 1 in 5,500 and 1 in 17,200 live births, respectively. A large variety of congenital defects, growth deficiencies, and intellectual disabilities are found in children with chromosomal aneuploidies, and these present life-long challenges to families and societies[3]. For these reasons, much effort has been devoted to detecting chromosome abnormalities during early fetal life, at a time when therapeutic abortions can be offered as an option to prospective parents.

There are a variety of prenatal diagnostic tests that can indicate increased risk for fetal aneuploidy, although invasive tests such as amniocentesis or chorionic villus sampling are the current gold standard[4] and are associated with a non-negligible risk of fetal loss. More reliable, non-invasive tests for fetal aneuploidy have therefore long been sought. The most promising of these are based on the detection of fetal DNA in maternal plasma, as pioneered by Lo's group[5]. It has been demonstrated that massively parallel sequencing of libraries generated from maternal plasma can reliably detect chromosome 21 abnormalities[6,7]. In the most comprehensive study to date[8], 98.6% of fetuses with trisomy 21 were detected in maternal plasma, with a false positive rate of 0.2 percent. In an additional 0.8 percent of samples, the test failed to give a result. These exciting studies promise a new era of non-invasive prenatal testing.

Currently, almost half of trisomy 21 babies are born to mothers less than 35 years of age, as more than 80% of pregnant women are under 35[9,10]. Though the risk of invasive procedures is thought to outweigh the benefit of invasive testing for eligible young mothers, it is clear that the vast majority of births associated with chromosomal aneuploidies could be safely prevented with reliable non-invasive tests that could be safely administered to all pregnant women. Prenatal testing is an extraordinarily stressful exercise for pregnant mothers and their families, and the more rapid the process, the better.

To achieve this goal with circulating fetal DNA testing, decreases in cost and increases in throughput will be necessary. There are three major components of plasma DNA testing: preparation of DNA libraries for loading on the sequencing instrument, the sequencing of these libraries, and their analysis. The second component is being addressed by instrument manufacturers, who have made remarkable progress over the last few years. Potential improvements in the first and third components are the subject of the current study.

The only commercially available test for circulating fetal DNA aneuploidy involves the preparation of whole genome libraries and the analysis of a sufficient number of sequences on the relevant chromosomes to reliably detect small differences in copy number. The preparation of whole genome libraries involves several sequential steps, including end-repair, 5'-phosphorlyation, addition of a terminal dA nucleotide to the 3' ends of the fragments, ligation of the fragments to adapters, and PCR amplification of the ligated products, many of which require intervening purifications. The PCR products are then quantified and loaded on the sequencing instrument. Following the sequencing run, the tags are aligned to the human genome and assessed with Digital Karyotyping[11], i.e., the number of tags per genomic locus is used to construct a virtual karyotype. Another recently described test involves fewer, but still a large number of, steps to prepare libraries for sequencing[12].

There is a continuing need in the art to rapidly and non-invasively detect genetic abnormalities.

SUMMARY OF THE INVENTION

According to one embodiment of the invention a method is provided for testing a human for aneuploidy. A plurality of chromosomal sequences in a DNA sample from a human are amplified with a single pair of primers complementary to said chromosomal sequences to form a plurality of amplicons, wherein the plurality of amplicons are not identical, and wherein the plurality of amplicons include sequences on a query chromosome and sequences on a plurality of reference chromosomes. Reactions are performed to determine the nucleotide sequence of at least 3 nt of the plurality of amplicons. Amplicon nucleotide sequences are matched in silico to genomic sequences at genomic loci. Numbers of matching amplicons at individual genomic loci are counted. Numbers of amplicons matched to genomic loci on the query chromosome are compared to numbers of amplicons matched to genomic loci on the reference chromosomes.

According to another embodiment a method is provided for testing a human for DNA copy number changes. A plurality of chromosomal sequences in a DNA sample from a human are amplified with a single pair of primers complementary to the chromosomal seuqences to form a plurality of amplicons, wherein the plurality of amplicons are not identical, and wherein the plurality of amplicons include sequences in a query chromosomal region and sequences in a plurality of reference chromosomal regions. Reactions are performed to determine the nucleotide sequence of at least 3 nt of the plurality of amplicons. Amplicon nucleotide sequences are matched in silico to genomic sequences at genomic loci. Numbers of matching amplicons at individual genomic loci are counted. Numbers of amplicons matched to genomic loci in the query chromosomal region are compared to numbers of amplicons matched to genomic loci in the reference chromosomal regions.

A pair of primers is provided which is useful for analyzing human aneuploidy. A first primer comprises SEQ ID NO: 1 and a second primer comprising SEQ ID NO: 2.

A method of selecting primers is provided for use in detecting human aneuploidy. A pair of primers is identified in which the primers are complementary to a plurality of pairs of chromosomal segments that are separated by 3 to 10,000 nt of intervening sequence in a human genome. The intervening sequences are distributed on at least three human chromosomes. The pairs of chromosomal segments and their intervening sequence are amplified to form a population of amplicon molecules whose representation in the population reflects representation of the chromosomal segments and their intervening sequences in the human genome.

These and other embodiments which will be apparent to those of skill in the art upon reading the specification provide the art with new tools and methods for assessing genomic copy number sensitively and rapidly.

BRIEF DESCRIPTION OF THE DRAWINGS

FIGS. 1a-1d: Comparison of observed and predicted distributions of FAST-SeqS amplification products. (FIG. 1b) A density plot of the actual tag counts obtained in eight normal plasma DNAs. The 124 bp fragments are preferentially amplified compared to the 142 bp fragments. Inset: polyacrylamide gel of a representative FAST-SeqS sequencing library. Note that the amplification products contain an additional 121 bp of flanking sequence to facilitate sequencing (Supplementary Table 3).

FIGS. 2a-2c: Demonstration of FAST-SeqS reproducibility.

FIG. 3a-3b (Supp. FIG. 1) Further demonstration of FAST-SeqS reproducibility using different instruments, samples, and sequencing depth.

FIG. 4 (Supp. FIG. 2) Pilot mixing experiment of trisomy 21 and euploid DNA. Control peripheral blood white blood cell (WBC) DNA was analyzed alone (n=2) or when mixed with DNA from a patient with trisomy 21 at 5% (n=2), 10% (n=1), or 25% (n=1) levels. A tight correlation exists between the expected and observed fractions of extra chromosome 21 (r=0.997 by Pearson correlation test, n=6).

FIG. 6A-6B. (Supplementary Table 2) Sequencing characteristics of FAST-SeqS

DETAILED DESCRIPTION OF THE INVENTION

The inventors have developed a method that rapidly and non-invasively detects genetic abnormalities, in particular copy number abnormalities. We reasoned that the process in the commercially available test could be simplified if a defined number of fragments from throughout the genome could be amplified using a single primer pair, obviating the need for end-repair, terminal 3'-dA addition, or ligation to adapters. Furthermore, the smaller number of fragments to be assessed (compared to the whole genome) would streamline the genome matching and analysis processes. The method developed was capable of detecting trisomies in a reproducible fashion in pilot experiments. It has advantages over unbiased whole genome sequencing in ease of implementation, cost, analysis time, and throughput.

Our approach to achieving the goals was based on the use of specific primers that anneal to a subset of human sequences dispersed throughout the genome. We named this approach "Fast Aneuploidy Screening Test-Sequencing System (henceforth FAST-SeqS). For maximum utility, we sought to identify regions with enough similarity so that they could be amplified with a single pair of primers, but sufficiently unique to allow most of the amplified loci to be distinguished. To be compatible with the degraded DNA found in plasmas, we further required that the amplified sequences be ≤150 bp. Using the BLAST-Like Alignment Tool (BLAT) algorithm[13], we iteratively searched fragments of a small portion of chromosome 21 (~6.8 Mb) containing the Down's Syndrome critical region to identify suitable primer pairs, i.e., primer pairs that would amplify many distinct fragments of DNA from throughout the genome as well as throughout the Down's Syndrome critical region. Three such primer pairs were identified, and after testing these primers in silico (using In Silico PCR") as well as in pilot sequencing experiments, we found one of the three primer pairs (henceforth FAST-1) to be optimal (Online Methods). The FAST-1 primer pair was predicted to amplify subfamilies of long interspersed nucleotide elements (L1 retrotransposons) which, like other human repeats, have spread throughout the genome via retrotransposition, particularly in AT-rich regions[15]. As it is generally more difficult to uniformly amplify and sequence regions that vary widely in their GC content[8,16], we expected that this differential localization would work in our favor.

Any chromosome or chromosome region can be queried. Non-limiting examples of useful query chromosomes and regions are chromosome 21, chromosome 13, chromosome 18, the X chromosome, the Y chromosome, Down's Syndrome critical region on chromosome 21. The query and reference chromosomes may be nuclear. In some embodiments at least two, three, four, or five amplicons tested match a genomic sequence within a query chromosome or query region.

The amplicons may be relatively small so that the degraded nature of some samples is not an impediment to detection. The amplicons may be less than 1 kbp, less than 500 bp, less than 250 bp, less than 180 bp, less than 150 bp, less than 120 bp, less than 100 bp, or less than 50 bp. In one embodiment the pair of primers comprises a first and a second primer in which the first primer comprises SEQ ID NO: 1 and the second primer comprising SEQ ID NO: 2.

The DNA sample may come from any source, but preferably is from a mammal and more preferably is from a human. In certain embodiments the sample is from a gravid female and the DNA sample comprises maternal and fetal DNA. The DNA sample may be from plasma or from serum, for example. Other body fluids such as saliva, tears, sweat, lymph, urine, may be used. Tissue samples may be used as a source of DNA. Cord blood may be used as a source of DNA. Because fetal DNA is only a small fraction of maternal plasma DNA, maternal DNA could mask a fetal abnormality. Therefore a sufficient number of amplicons must be counted to detect fetal aneuploidy if present.

Although the amplicons may be larger, the entire amplicon need not be sequenced to identify an amplicon. In some embodiments as few as 4, 5, 6, 7, 8, 9, 10, 11, 12, 13, 14, 15, 16, 17, 18, 19, 20, 21, 22, 23, 24, 25, 26, 27, 28, 29, or 30 nt of nucleotide sequence is determined of the plurality of amplicons. More may be determined if desired.

Useful primer pairs may be complementary to sequences that are distributed on at least 4, 5, 6, 7, 8, 9, 10, 11, 12, 13, 14, 15, 16, 17, 18, 19, 20, 21, 22, or 23 human chromosomes. The complementary sequences may be separated by at least 3, 4, 5, 6, 7, 8, 9, 10, 11, 12, 13, 14, 15, 16, 17, 18 or more nt.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Methods
Primer Selection

We began by searching a ~6.8 Mb region of chromosome 21 containing the Down's Syndrome critical region (hg19[17] coordinates 35,888,786 to 42,648,523) for sequence blocks of ~150 bp that were similar but not identical to those present on all chromosomes. Using 150 bp sliding windows incremented by 50 bp (135,186 sequences of 150 bp in length), we queried sequences with the BLAST-Like Alignment Tool (BLAT) algorithm[13] to identify such blocks. We also required that at least three of the blocks were present on chromosome 21 in addition to the one within the ~6.8 Mb region described above.

Out of the 135,186 queried blocks, we found only 56 that met the following criteria:
contained at least 11 variant bases from the query sequence, to aid in distinguishing amplified loci;
contained no more than 30 variant bases from the query sequence, to increase the chance of uniform amplification; and
spanned no more than a total of 180 bases, to be compatible with the analysis of degraded DNA.

We then manually scanned the BLAT alignments of these 56 blocks to search for those that had highly similar 5' and 3' ends. At least three of the 56 sequences met our criteria and we designed primers for them. In Silico PCR[14] verified that each theoretical primer pair would amplify many distinct sequences from every nuclear chromosome.

Ascertainment of Amplification Product Uniqueness.

Figure 1A:
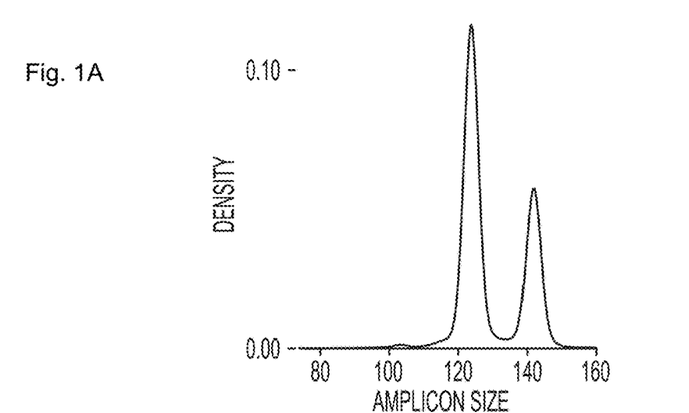
(FIG. 1a) A density plot of the expected distribution of fragment lengths, with peaks at 124 and 142 bp.
Figure 1B:
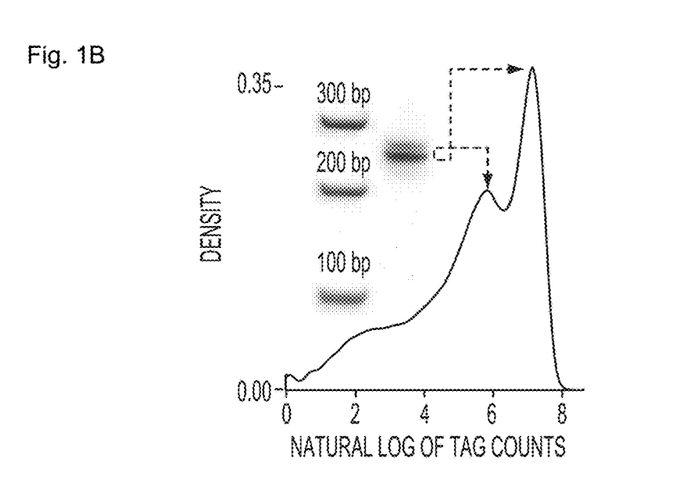

Sequences that were too similar could pose a problem during alignment because of the inevitable errors introduced during library preparation or sequencing. We therefore wrote a custom script to assess how many distinct sequences would remain after allowing one, two, or three errors in each ~150 bp sequence. The theoretical amplification products of one primer pair (FAST-1) greatly outperformed the other two, and the superiority of FAST-1 was confirmed in pilot sequencing experiments. In Silico PCR[14] predicted a bimodal distribution of PCR fragments, and this was confirmed by size separation of the amplified PCR products on a polyacrylamide gel and through the observed distribution of counts per position (FIG. 1b).

Templates.

Control DNA was obtained from normal spleen, peripheral blood white blood cells (WBCs), or plasma (Supplementary Table 1). Fibroblast DNA from five individuals with trisomy 21 (NA02767, NA04616, NG05120, NG05397, and NG07438), two with trisomy 18 (NA03623 and NG12614), and one with trisomy 13 (NA03330) were purchased from the Coriell Institute for Medical Research (Camden, New Jersey). A total of 33 ng of DNA was used for each experiment. All templates were quantified by OD, except for the mixing experiments in which the templates were quantified by Digital PCR[20] to achieve a more accurate estimate of concentration.

Sequencing Library Preparation.

The significant savings in time in FAST-SeqS is due to the replacement of a traditional whole genome amplification library preparation with an amplification using a single primer pair. Templates were amplified with FAST-1 primers as described by Kinde et al[21] in which individual template molecules are tagged with a unique identifier DNA sequence. Though the unique identifier sequences turned out to be not necessary for FAST-SeqS (see Precise template counting section below), we included them in the initial experimental design and continued to use them once they were observed to provide robust PCR products in our initial experiments. Briefly, the FAST-1 amplification primers each contained a different 5' universal primer sequence (UPS) followed by the sequences allowing amplification of the repeated elements described above (Forward: ACACAGG-GAGGGGAACAT; SEQ ID NO: 1; Reverse: TGC-CATGGTGGTTTGCT; SEQ ID NO: 2) (Supplementary Table 3). Additionally, the forward primer contained a stretch of 16-20 degenerate bases immediately 3' to its UPS (Supplementary Table 3). PCR was performed using Phusion Hot Start II Polymerase (Thermo Scientific, cat. no. F-549L) in 1×Phusion HF buffer, 0.5 µM each primer, and two units of polymerase in a total of 50 µL under the following cycling conditions: 98° C. for 120 s, followed by two cycles of 98° C. for 10 s, 57° C. for 120 s, and 72° C. for 120 s. The initial amplification primers were removed with AMPure XP beads (Beckman Coulter Genomics, cat. no. A63880) according to the manufacturer with the exception that the beads were added at only 1.4× the PCR volume and the elution volume was reduced to 10 uL of TE. The elution was used directly for a second round of amplification using primers that annealed to the UPS site introduced by the first round primers and that additionally contained the 5' grafting sequences necessary for hybridization to the Illumina flow cell (Supplementary Table 3). Further, we introduced one of five indexes ("barcodes") (Supplementary Table 3) to each sample in the reverse primer to later allow multiplexed sequencing. The second round of PCR was performed using Phusion Hot Start II Polymerase in 1×Phusion HF buffer, 0.5 µM each primer, and two units of polymerase in a total of 50 µL under the following cycling conditions: 98° C. for 120 s, followed by 13 cycles of 98° C. for 10 s, 65° C. for 15 s, and 72° C. for 15 s. Amplification products were again purified with AMPure XP beads and were quantified by spectrophotometry, real time PCR or on an Agilent 2100 Bioanalyzer; all methods of quantification yielded similar results. Oligonucleotides were purchased from IDT (Coralville, Iowa).

Data Analysis Overview

As opposed to traditional whole genome amplification libraries, where the vast majority of tags align to the genome in unique positions and thus each tag needs an independent alignment, FAST-SeqS yields sequences that aligned to an average of only 21,676 positions; Supplementary Table 2). The number of positions to which the sequences aligned varied little compared to the range of sequence data obtained across all experiments. Though the number of uniquely aligned tags per experiment spanned a 12-fold range (1,343,382 to 16,015,347) the number of positions varied only by 0.25-fold (range: 18,484 to 24,562 positions; Supplementary Table 2). Raw reads from all experiments (Supplementary Table 2) can be downloaded from the domain sagenet.org, subdomain fast, document fast.htm.

Sequence tag Filtering and Alignment

Thirty-seven base sequence tags passing the Illumina chastity filter and containing at least three correct terminal bases of the amplification primer were filtered for quality by masking any base with a quality score <20 with an N using a custom script. Thus, tags with low quality bases were given the opportunity to align by considering only their most reliable bases. After quality masking, only the distinct sequences were aligned to the human genome (hg19[17]) using Bowtie 0.12.7[18]. When building the reference index for Bowtie, we included unresolved or unplaced contigs[22] to ensure the most accurate alignments. Sequences that aligned uniquely with up to one mismatch (using the flags -m 1 and -v 1, respectively) were retained and their alignments were matched back to the original data. An average of 38% of tags across all samples could be uniquely assigned to a genomic position (range: 31% to 45%; Supplementary Table 2).

Estimating the Distribution of Sequenced Fragments.

After confirming the in silico prediction of a primarily bimodal distribution of FAST-SeqS amplification products by gel electrophoresis, we investigated whether the counts of sequenced fragments that aligned to unique positions were similarly distributed. Though we only sequenced 37 bases, we could estimate the relative size of each tag from In Silico PCR[14] and its unique position in the genome. This exercise could provide additional evidence that the actual amplification products matched those that were predicted and could alert us to any amplification bias (see Normalization section below).

First, we transformed the tag counts per uniquely aligned position to a log scale, a transformation frequently performed to this class of data to induce symmetry[23]. We performed this transformation for each group of experiments (e.g., from eight normal plasma samples analyzed in the same instrument run; Supplementary Table 2). Next, we used a nonparametric method to estimate a smoothened distribution (a kernel density estimator, implemented in R[24] using the density function), which made it straightforward to visualize the modality of our data. After plotting the distribution using ggplot2[25] (an R[24] package), we observed that each group of experiments showed a similar clustering of tag counts per position, consistent with a primarily bimodal distribution with a negative skew. A representative plot is displayed in FIG. 1b.

Normalization.

Massively parallel sequencing will generate a different number of sequence tags from each sample, as well as from different sequencing runs of the same sample, due to stochastic and experimental variations. Thus, it is essential to normalize the data to make meaningful comparisons of the type used here. Although it would be most straightforward to simply express tag counts as a fraction of the total number of tags sequenced in an experiment, this normalization is too simplistic and is highly susceptible to systemic biases that frequently plague next generation sequencing of both DNA and RNA templates, and these are routinely used in digital karyotyping analyses such as that used for the diagnosis of trisomy 21[8,16].

Because of the bimodal size distribution of the amplicons obtained with the FAST-1 primer pair, we predicted that the majority of bias in FAST-1 amplifications would be due to the potential over-representation of the smaller-sized fragments. This bias could either occur during library preparation or during solid-phase bridge PCR on the Illumina flow cell. We found that an appropriate normalization for this distribution could be obtained using the quantile method[19], used extensively within the microarray community. By organizing our data into a list of positions (equivalent to probes in microarray data), each associated with a tag count (equivalent to intensities in microarray data), we were able to apply standard quantile normalization to FAST-SeqS data. To best approximate the microarray data format, we chose to only analyze positions that were shared within each experimental group (e.g., the data from eight normal plasma samples). As the FAST-1 primers amplified a highly reproducible set of positions, this generally only eliminated <1% of the data. To maximize reproducibility, we excluded positions aligning to unresolved or unplaced contigs and those aligning to sex chromosomes, although inclusion of these chromosomes only marginally increased variability between experiments (e.g., in eight normal plasma samples, the maximum z-score from any chromosome rose from 1.9 to 2.3). The inclusion of sex chromosomes could be useful for other applications, such as detecting aneuploidies involving chromosome X or determining the gender of a sample (i.e., by the presence or absence of sequences aligning to chromosome Y).

We implemented the quantile normalization[19] for each experimental group (each of which contained multiple samples; Supplementary Table 2) by performing the following steps:

generating a sorted array of tag counts representing each position for every sample (all of equal length as only the shared positions in each experiment were analyzed);

combining these sorted arrays into a 2×2 matrix, where each experiment is represented in its own column and the shared positions constitute the rows;

replacing an individual sample's count with the mean count for all samples at that particular row; and re-sorting the counts back to their original order.

The distribution of our data was always negatively skewed (see FIG. 1b for a representative example). We excluded the positions falling within the left tail of each experiment's distribution (the positions containing the smallest number of tags) from our analysis by:

estimating the distribution of normalized values as described above;

determining the inflection point between the two peaks of the bimodal distribution; and considering the positions that had a relative density below the inflection point as the left tail.

Once the left tail was determined and positions within it discarded, the quantile normalization was repeated. Through this process, each sample within an experimental group had the same sum total of tags and an identical distribution of counts, so direct comparisons could be made. We automated the quantile normalization in $R^{24}$. The entire normalization procedure routinely took less than a few minutes to complete.

Quantitative Determination of Aneuploidy Status.

A common method of determining the aneuploidy status of a particular sample in Digital Karyotyping-based[11] assays is by comparison of z-scores[6,8,26]. Through this method, one determines the mean and standard deviation of tag counts lying within a chromosome of interest in a group of reference samples (e.g., samples with known euploid content), and then creates a standardized score (i.e., z-score) for a chromosome of interest for each sample as follows: z-score$_{i,chrN}$=(chrN$_i$-$\mu_{chrN}$)/sd$_{chrN}$, where i represents the sample to be standardized, chrN represents the normalized tag count of the sample's chromosome, and $\mu_{chrN}$ and sd$_{chrN}$ represent the mean and standard deviation of the normalized tag counts, respectively, of chrN in the reference group. When all samples are standardized in this way, outliers are easily detected because they have a z-score>3.0. This indicates that the normalized tag count of the outlier exceeds the mean of the reference group by at least three standard deviations.

Precise Template Counting.

Finally, we evaluated whether precisely counting template molecules could further increase reproducibility. By incorporating 16-20 degenerate bases at the 5' end of one of the two FAST-1 primers (Supplementary Table 3), it is possible to uniquely identify each template molecule giving rise to a PCR product[21]. This could potentially increase accuracy by minimizing the possibility that the same template molecule was counted more than once in the final tally for each chromosome. We found that this enhancement did not significantly alter the consistency of normalized counts per chromosome among the eight normal plasma samples: the maximum z-score for any chromosome was slightly increased from 1.9 to 2.0. By performing a two-tailed t-test on the absolute values of the z-scores for all autosomes comparing analysis methods, we found no statistically significant difference between the two methods (p=0.759, n=22×8 for each group).

EXAMPLE 2

Figure 1C:
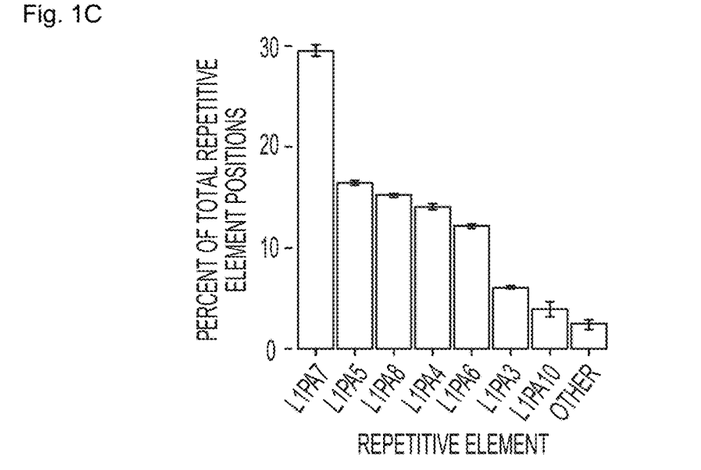
(FIG. 1c) The average representation of L1 retrotransposons within repetitive DNA in eight normal plasma samples. Roughly 97% of tags align to positions representing only seven L1 retrotransposons.
Figure 1D:
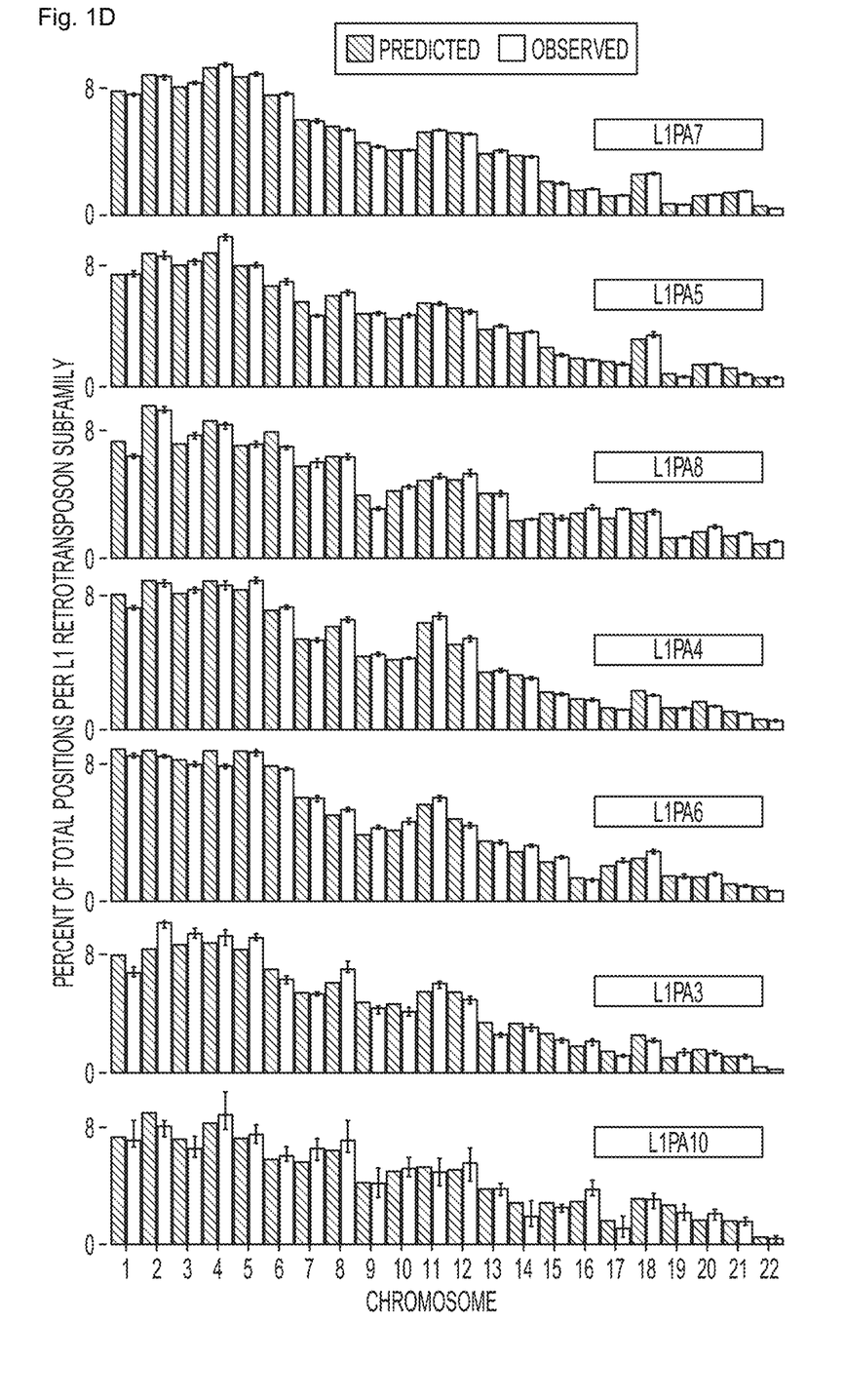
(FIG. 1d) A detailed examination of the observed distribution from eight normal plasma DNAs compared with the distribution of each of the seven L1 retrotransposons predicted by RepeatMasker. Error bars in each panel depict the range.

As an initial test of the performance of FAST-SeqS, we examined the representation of each autosome in the plasma DNA of seven normal females, including one biologic replicate (Supplementary Table 1). Using only 37 cycles of sequencing in one-quarter of a lane on an Illumina HiSeq 2000 instrument, we recovered an average of 31,547,988 high quality tags per individual (range: 27,179,424 to 36,0418,017 tags; Supplementary Table 2). An average of 35% of these tags (range: 31 to 37%) could be uniquely mapped to one of an average of 23,681 unique chromosomal positions (range: 22,589 to 24,562 positions) when allowing up to one mismatch during alignment to hg19[17] using Bowtie[18]. The theoretical in silico (FIG. 1a) and observed distribution of tag counts (FIG. 1b) both showed a bimodal distribution of sizes. Of the uniquely aligned tags, 99.1% aligned to positions predicted to be repetitive DNA by RepeatMasker (website at subdomain www and domain RepeatMaker and top level domain org), 97.5% of which fell into just seven L1 retrotransposon subfamilies (FIG. 1c). Additionally, the distribution of each subfamily agreed with that predicted by RepeatMasker (FIG. 1d). Because tag alignment to a discrete set of chromosomal positions is simpler than alignment to the entire genome, the post-sequencing analysis process was very rapid. In fact, this mapping plus subsequent statistical analysis could be completed in less than 30 min per sample with a single computer housing two six-core CPUs (Intel Xeon X5680).

Figure 2A:
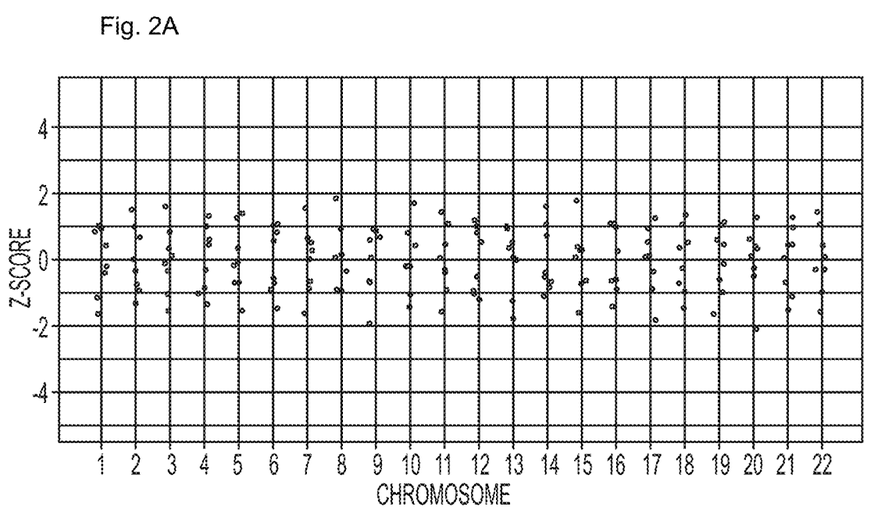
(FIG. 2a) Calculated z-scores for each autosome from eight normal plasma DNA samples. No chromosome had a z-score >3.0 (range: −2.1 to 1.9).

Most importantly, the relative fraction of tags mapping to each chromosome was remarkably similar among the individual samples after normalizing[19] to compare chromosome tag counts among different samples (Online Methods). In particular, the fraction of tags that matched to any of the autosomes in any of the eight samples studied never deviated from the average by a z-score>3.0 (FIG. 2a). Of particular note, the maximum z-scores observed among the eight samples for chromosomes 21, 18, and 13 were 1.3, 1.4, and 1.0, respectively.

EXAMPLE 3

Figure 3A:
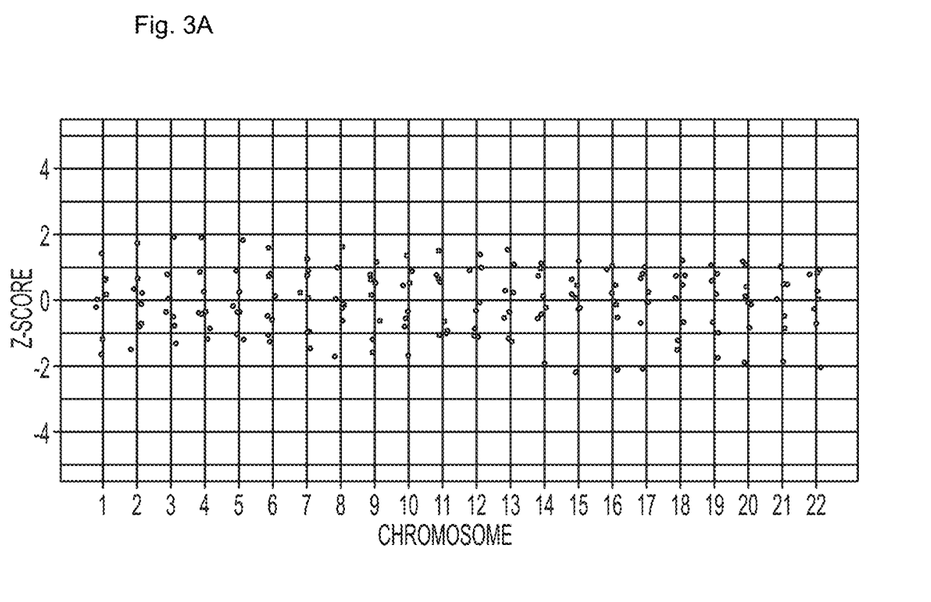
(FIG. 3a) Matched peripheral blood white blood cell (WBC) DNA from eight samples whose plasma DNA was sequenced in FIG. 2a was also sequenced on one-quarter of an Illumina HiSeq 2000 lane. Plotted are the calculated z-scores for each autosome. No chromosome had a z-score >3.0 (range: −2.2 to 1.9).

We next studied the reproducibility of chromosome representation in two additional experiments employing different types of samples, different instruments, and different depths of sequencing. In the first experiment, we analyzed DNA from peripheral blood white blood cells (WBCs) from the same seven individuals who contributed plasma. Four samples were sequenced on a single lane of an Illumina HiSeq 2000, yielding a mean of 10,835,559 uniquely aligned tags per sample (range: 4,905,067 to 16,015,347 tags). The maximum z-scores for any of the samples were 1.0, 1.2, and 1.6 for chromosomes 21, 18, and 13, respectively (Supplementary FIG. 1a).

EXAMPLE 4

Figure 3B:
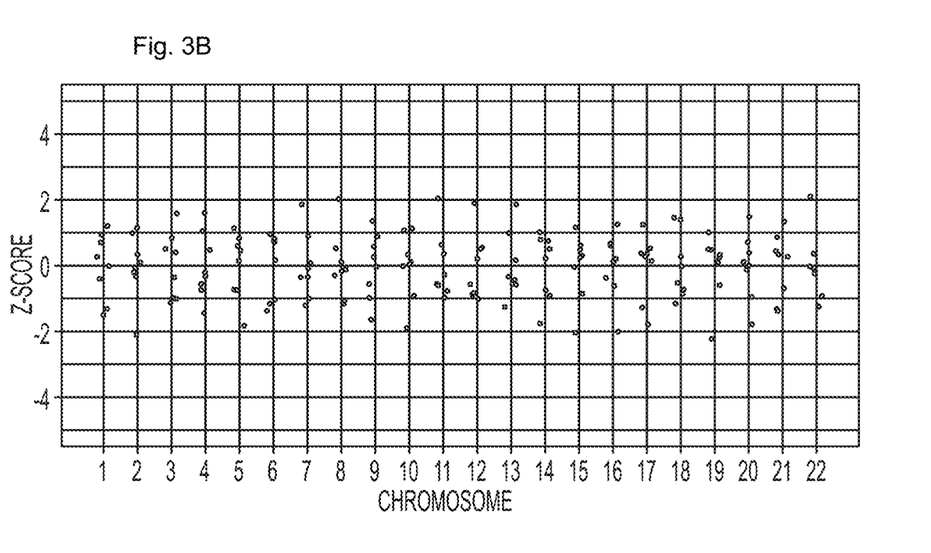
(FIG. 3b) Eight samples of either splenic or WBC DNA were sequenced on one-half of an Illumina GA IIx lane, designed to yield less tags than the aforementioned plasma and WBC samples (FIG. 2a and (a)). Displayed are the z-scores calculated for each autosome. Despite three-fold less sequencing, no chromosome had a z-score >3.0 (range: −2.2 to 2.1).

In the next experiment, we analyzed splenic or WBC DNA from an additional eight individuals using one-half of a lane of an Illumina GA IIx instrument per sample (Supplementary Table 2). We obtained a mean of 4,013,951 uniquely aligned tags per sample (range: 2,847,661 to 4,645,608 tags). Despite almost 3-fold less sequencing, the maximum z-scores among the samples were still only 1.3, 1.5, and 1.9 for chromosomes 21, 18, and 13, respectively, well below the widely used cutoff of 3.0 (Supplementary FIG. 1b).

Figure 2B:
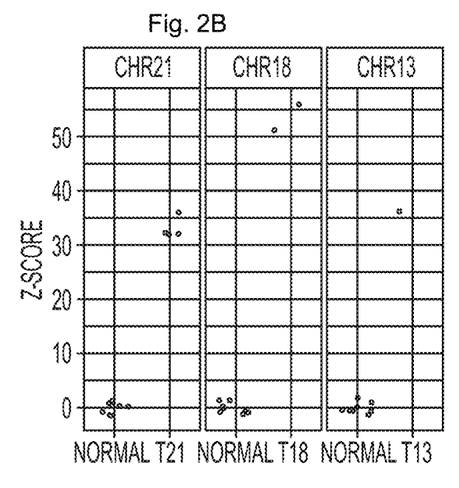
(FIG. 2b) Comparison of z-scores from patients with trisomy 21 (n=4), trisomy 18 (n=2), and trisomy 13 (n=1) with eight normal spleen or WBC DNAs. The z-scores displayed represent the relevant chromosome for the comparison. The maximum z-score observed for any of the compared normal chromosomes was 1.9 (chr13).

Given the tight distributions of tags evident in FIG. 2a, we expected it would be straightforward to distinguish the DNA of patients with trisomies from those of normal individuals with euploid chromosome constitutions. The data depicted in FIG. 2b demonstrate that this expectation was realized in each of four patients with trisomy 21. The z-scores among these trisomy 21 patients ranged from 32 to 36, while the maximum z-score among eight normal individuals was 1.3. Similarly, the z-scores of DNA from two patients with trisomy 18 and one from trisomy 13 were 51, 56, and 36, respectively, far exceeding the maximum z-scores for these chromosomes in normal individuals (FIG. 2b).

EXAMPLE 5

Figure 2C:
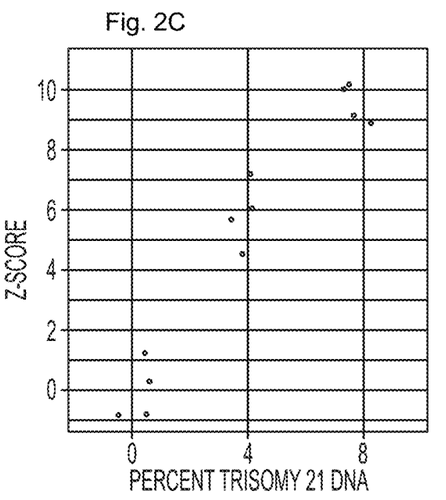
(FIG. 2c) Control WBC DNA was analyzed alone (z-score range: −0.8 to 1.3) or when mixed with DNA from a patient with trisomy 21 at 4% (z-score range: 4.5 to 7.2) or 8% (z-score range: 8.9 to 10.) levels. Each experiment in (FIG. 2c) was performed in quadruplicate.
Figure 4:
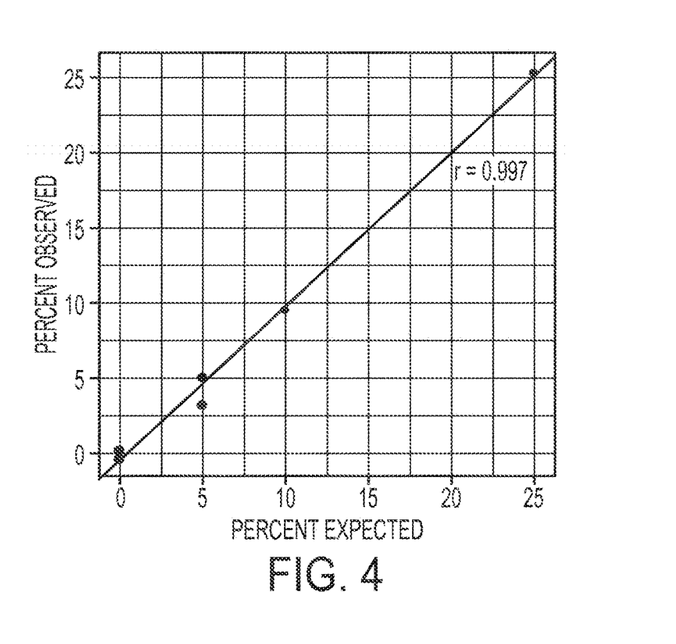
Figure 5:
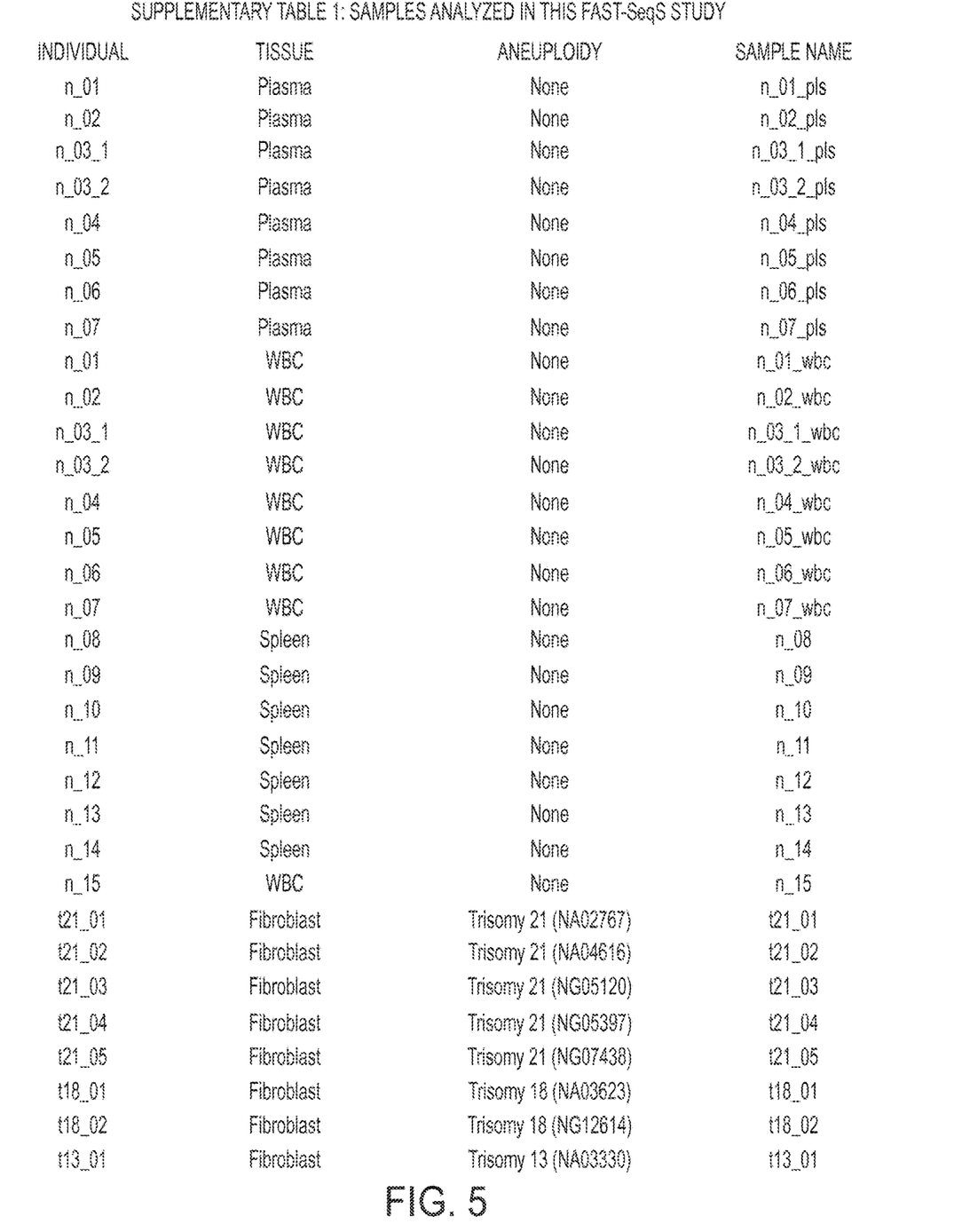
FIG. 5. (Supplementary Table 1.) Samples analyzed in this FAST-SeqS study
Figure 6B:
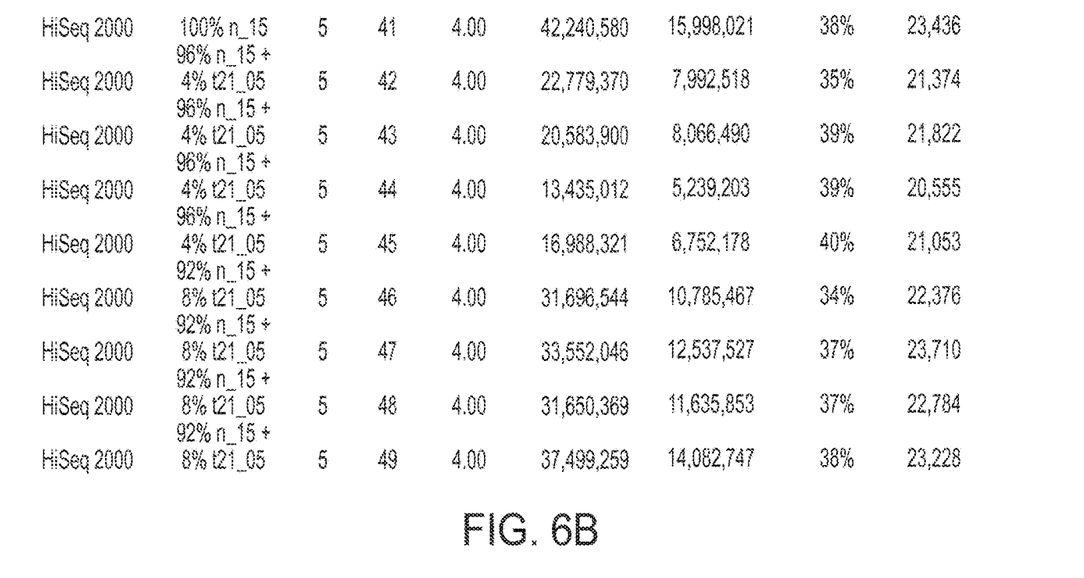
Figure 7:
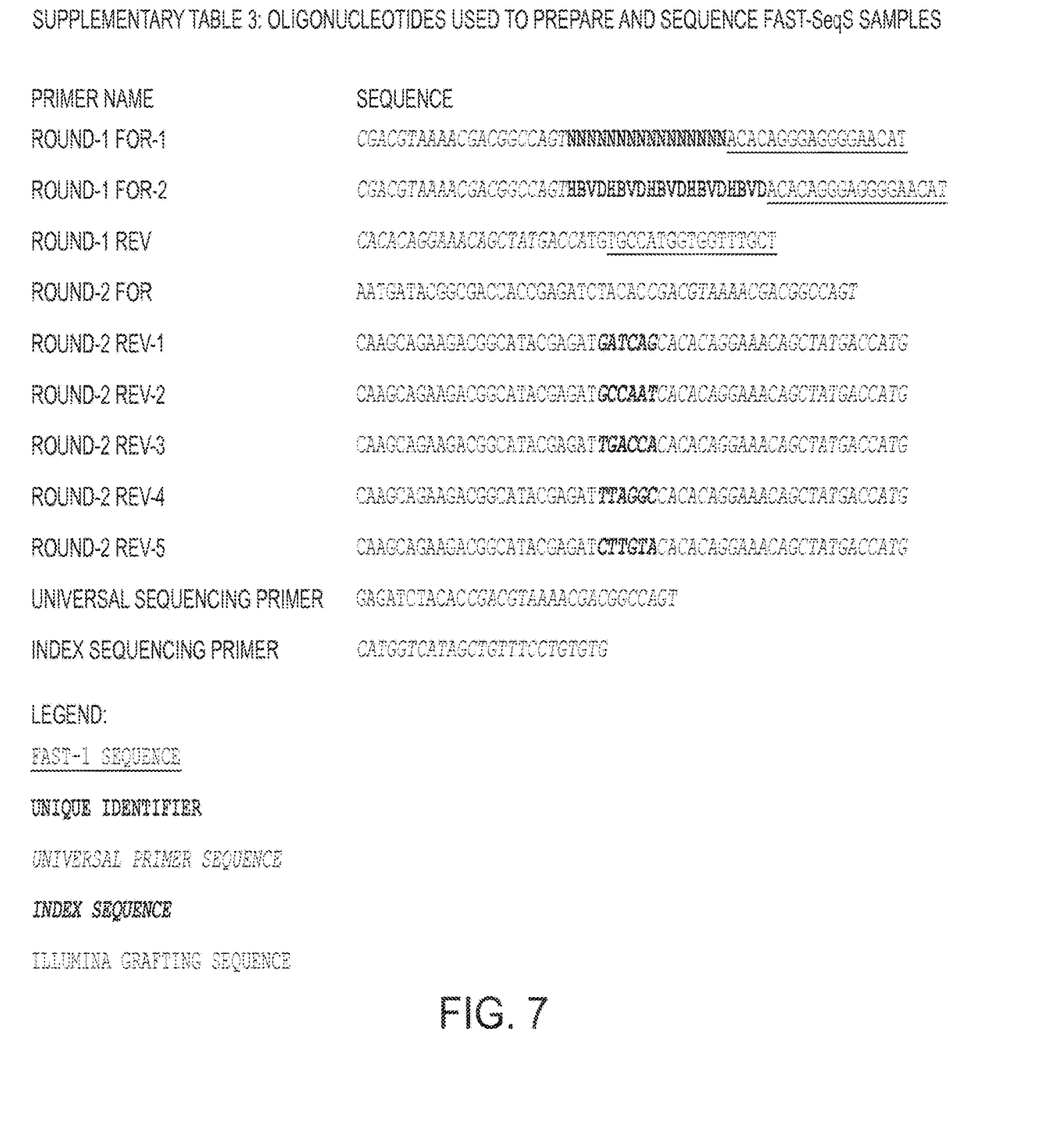
FIG. 7. (Supplementary Table 3.) Oligonucleotides used to prepare and sequence FAST-SeqS samples (SEQ ID NO: 4-14 consecutively)
Figure 8:
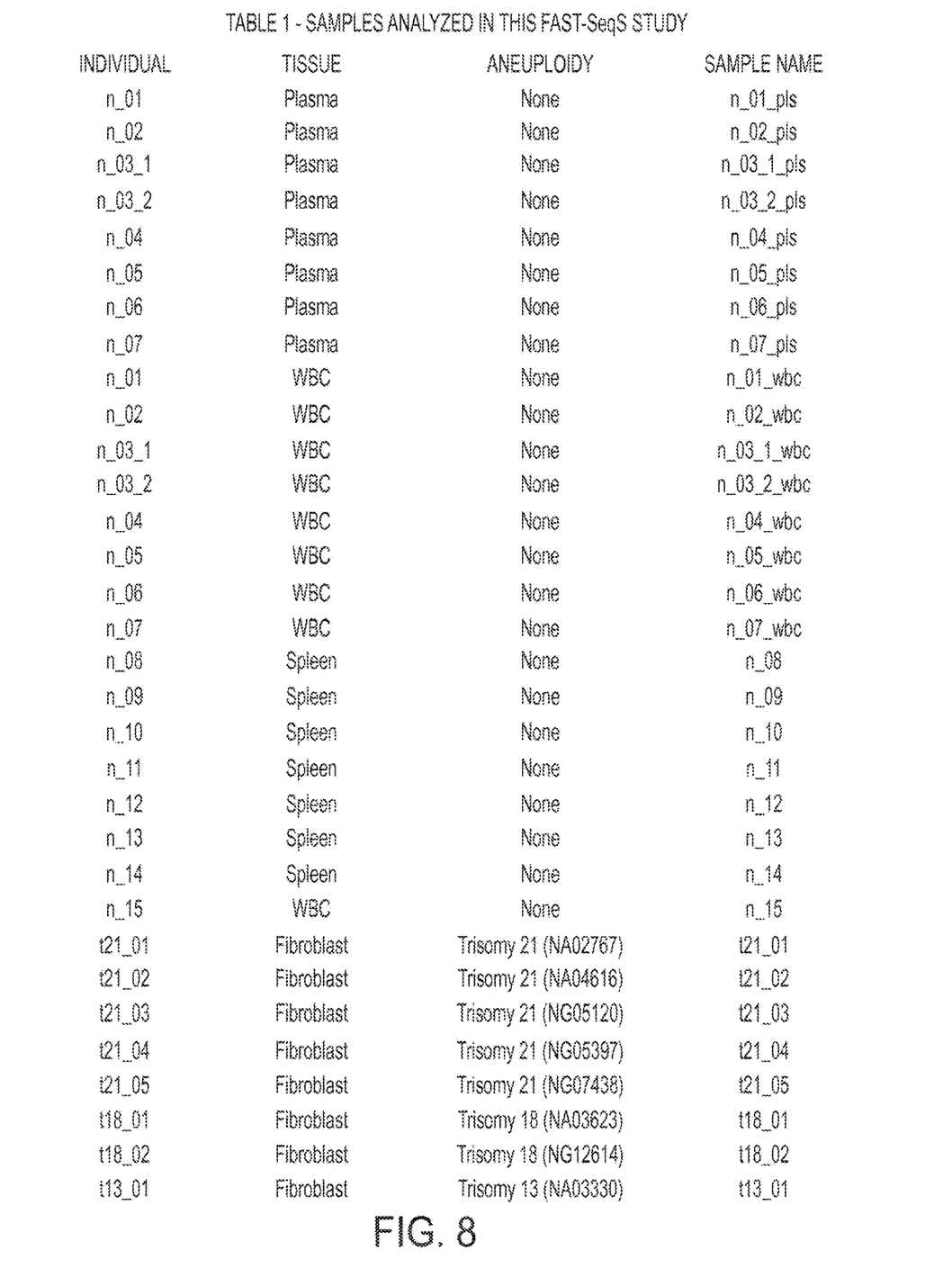
FIG. 8. (Table 1) Samples analyzed in this FAST-SeqS study

Fetal DNA accounts for a geometric mean of 13.4% of maternal DNA, depending largely on maternal weight rather than gestational age[8]. To investigate whether FAST-S eqS could distinguish samples that contained mixtures of disomic and trisomic DNA, we performed mixing experiments using DNA from patients with trisomy 21 and normal individuals. In a first experiment of this type, we mixed 5% (n=2), 10% (n=1), and 25% (n=1) trisomy 21 DNA into normal WBC DNA alongside two controls (Supplementary FIG. 2), and found a tight correlation between the expected and observed fractions of extra chromosome 21 (r=0.997 by Pearson correlation test, n=6). In a second experiment, we evaluated mixtures that contained 4% or 8% trisomy 21 DNA. As shown in FIG. 2c, there was a clear distinction between the samples containing 4% trisomy 21 DNA vs. those from normal individuals (p=$2 \times 10^4$ as determined by two-tailed t-test, n=4 in each group). The samples containing 8% trisomy 21 DNA were of course even more easily distinguishable (p=$4 \times 10^{\oplus 6}$ when compared to the euploid group and p=$1 \times 10^{-3}$ when compared to the 4% trisomy 21 samples, both by two-tailed t-test with n=4 for each group).

REFERENCES

The disclosure of each reference cited is expressly incorporated herein.
1. LYF Hsu, in *Genetic Disorders and the Fetus*, edited by A Milunsky (The Johns Hopkins University Press, Baltimore, 1998), pp. 179.
2. M. Staebler, C. Donner, N. Van Regemorter et al., *Prenat Diagn* 25 (7), 567 (2005).
3. K. L. Jones, *Smith's recognizable patterns of human malformation*, 6 ed. (Elsevier Saunders, Philadelphia, 2006).
4. American College of Obstetricians and Gynecologists, Obstet Gynecol 110 (6), 1459 (2007).
5. Y. M. Lo, M. S. Tein, T. K. Lau et al., *Am J Hum Genet* 62 (4), 768 (1998).
6. R. W. Chiu, K. C. Chan, Y. Gao et al., *Proc Natl Acad Sci USA* 105 (51), 20458 (2008).
7. H. C. Fan, Y. J. Blumenfeld, U. Chitkara et al., *Proc Natl Acad Sci USA* 105 (42), 16266 (2008).
8. G. E. Palomaki, E. M. Kloza, G. M. Lambert-Messerlian et al., *Genet Med* 13 (11), 913 (2011).
9. J. Cleary-Goldman, F. D. Malone, J. Vidaver et al., *Obstet Gynecol* 105 (5 Pt 1), 983 (2005).
10. R. G. Resta, *Am J Med Genet A* 133A (1), 31 (2005).
11. T. L. Wang, C. Maierhofer, M. R. Speicher et al., *Proc Natl Acad Sci USA* 99 (25), 16156 (2002).
12. A. B. Sparks, E. T. Wang, C. A. Struble et al., *Prenat Diagn* (2012).
13. W. J. Kent, *Genome Res* 12 (4), 656 (2002).
14. R. M. Kuhn, D. Karolchik, A. S. Zweig et al., *Nucleic Acids Res* 35 (Database issue), D668 (2007).
15. A. F. Smit, *Curr Opin Genet Dev* 9 (6), 657 (1999).
16. H. C. Fan and S. R. Quake, *PLoS One* 5 (5), e10439 (2010).
17. P. A. Fujita, B. Rhead, A. S. Zweig et al., *Nucleic Acids Res* 39 (Database issue), D876 (2011).
18. B. Langmead, C. Trapnell, M. Pop et al., *Genome Biol* 10 (3), R25 (2009).
19. B. M. Bolstad, R. A. Irizarry, M. Astrand et al., *Bioinformatics* 19 (2), 185 (2003).
20. B. Vogelstein and K. W. Kinzler, *Proc Natl Acad Sci USA* 96 (16), 9236 (1999).
21. I. Kinde, J. Wu, N. Papadopoulos et al., *Proc Natl Acad Sci USA* 108 (23), 9530 (2011).
22. E. S. Lander, L. M. Linton, B. Birren et al., *Nature* 409 (6822), 860 (2001).
23. J. Tukey, *Exploratory Data Analysis*. (Addison-Wesley, Reading, Massachusetts, 1977).
24. R Development Core Team, R: A language and environment for statistical computing (R Foundation for Statistical Computing, 2011).
25. H. Wickham, *ggplot2: elegant graphics for data analysis*. (Springer, New York, 2009).
26. M. Ehrich, C. Deciu, T. Zwiefelhofer et al., *Am J Obstet Gynecol* 204 (3), 205 e1 (2011).

We claim:
1. A method of detecting the presence or absence of aneuploidy, comprising:
   a) contacting a sample comprising plasma DNA from a human patient with a single primer pair, wherein said primer pair comprises a first primer and a second primer,
      wherein both said first primer and said second primer are designed to anneal to long interspersed nucleotide elements (LINEs) present on a reference set of all twenty-two autosome human non-aneuploid chromosomes that would generate, during amplification, an expected distribution for said twenty-two autosome human non-aneuploid chromosomes,
      wherein said plasma DNA comprises at least a portion of all twenty-two autosome patient chromosomes;
   b) amplifying, using polymerase chain reaction, at least a portion of said plasma DNA using the single primer pair, whereby a plurality of amplicons from said LINEs are produced,
      wherein said plurality of amplicons are distinct from one another,
      wherein each of said plurality of amplicons is less than 180 bp in length; and
      wherein said plurality of amplicons comprise at least two amplicons from each of said twenty-two autosome patient chromosomes;
   c) sequencing at least 5 nucleotides of each of the amplicons in the plurality of amplicons;
   d) aligning in silico the sequenced amplicons from each of said twenty-two autosome patient chromosomes to said reference set of all twenty-two autosome human non-aneuploid chromosomes in order to produce a query distribution for each of said twenty-two autosome patient chromosomes,
      wherein said query distribution comprises a normalized count of the number of sequenced amplicons at each position where they align to said reference set of all twenty-two autosome human non-aneuploid chromosomes; and
   e) identifying:
      i) the presence of aneuploidy based upon finding at least one normalized count difference between said query distribution for at least one of said twenty-two autosome patient chromosomes and said expected distribution for a corresponding at least one of said twenty-two autosome human non-aneuploid chromosomes, or ii) the absence of aneuploidy based upon not finding at least one normalized count different difference between said query distribution and said expected distribution.

2. The method of claim 1, wherein said sequencing at least 5 nucleotides of each of the amplicons comprises sequencing at least 15 nucleotides of each of the amplicons in the plurality of amplicons.

3. The method of claim 1, wherein the presence of aneuploidy is identified in the sample.

4. The method of claim 1, wherein the absence of aneuploidy is identified in the sample.

5. The method of claim 1, wherein the average length of the plurality of amplicons is less than 150 bp.

6. The method of claim 1, wherein the sample is maternal plasma and the plasma DNA comprises fetal chromosomes.

7. The method of claim 1, wherein unique sequence tags are incorporated at a 5' end of the primers.

8. The method of claim 1, wherein, in step e): i) said at least one of said twenty-two autosome patient chromosomes comprises all twenty-two autosome patient chromosomes, and ii) said corresponding at least one of said twenty-two autosome human non-aneuploid chromosomes comprises all twenty-two autosome human non-aneuploid chromosomes.

9. The method of claim 1, wherein said plasma DNA is not ligated to adapters.

10. The method of claim 1, wherein said normalized count of the number of sequenced amplicons at each position where they align to said reference set of all twenty-two autosome human non-aneuploid chromosomes, and wherein said expected distribution comprises corresponding Z-scores for said at least one of said twenty-two autosome human non-aneuploid chromosomes.

11. The method of claim 1, wherein, in step e): i) said at least one of said twenty-two autosome patient chromosomes comprises chromosomes 21, 13 and 18, and ii) said corresponding at least one of said twenty-two autosome human non-aneuploid chromosomes comprises chromosomes 21, 13, and 18.

12. The method of claim 1, wherein said plurality of amplicons comprise at least 18,484 non-identical amplicons.

* * * * *

UNITED STATES PATENT AND TRADEMARK OFFICE
CERTIFICATE OF CORRECTION

Page 1 of 1

PATENT NO. : 12,116,628 B2
APPLICATION NO. : 17/483537
DATED : October 15, 2024
INVENTOR(S) : Bert Vogelstein et al.

It is certified that error appears in the above-identified patent and that said Letters Patent is hereby corrected as shown below:

On the Title Page

In Column 2, under "OTHER PUBLICATIONS" on Line 9, please delete "AOG.Ob013e31824fb482." and insert -- AOG.0b013e31824fb482.--, therefor.

In Column 2, under "OTHER PUBLICATIONS" on Line 11, please delete "oligonucleolide" and insert -- oligonucleotide --, therefor.

In the Claims

Claim 10: In Column 14, Line 10, delete "chromosomes," and insert -- chromosomes comprise Z-scores, --, therefor.

Signed and Sealed this
Seventeenth Day of December, 2024

Derrick Brent
*Acting Director of the United States Patent and Trademark Office*